United States Patent [19]

Lee et al.

[11] 4,440,929

[45] Apr. 3, 1984

[54] IMIDAZOQUINOXALINE COMPOUNDS

[75] Inventors: Thomas D. Lee, Scarsdale, N.Y.; Richard E. Brown, East Hanover, N.J.

[73] Assignee: USV Pharmaceutical Corporation, Tarrytown, N.Y.

[21] Appl. No.: 362,713

[22] Filed: Mar. 29, 1982

Related U.S. Application Data

[63] Continuation-in-part of Ser. No. 283,717, Jul. 16, 1981, abandoned.

[51] Int. Cl.³ .............. C07D 487/04; A61K 31/495; C07D 233/90; C07D 405/10
[52] U.S. Cl. .................................. 544/346; 544/343; 548/336; 548/337; 548/343; 424/250
[58] Field of Search ............................... 544/346, 343

[56] References Cited

PUBLICATIONS

Kollenz, Chem. Abs. 78, 16132r (1972).
Van Nispen, Tet. Letters 3723–26 (1980).

Primary Examiner—Mark L. Berch

[57] ABSTRACT

Provided are imidazoquinoxalines of the structures:

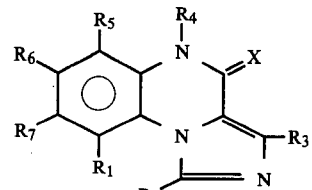

and

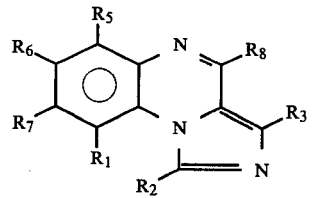

wherein $R_1$, $R_5$, $R_6$ and $R_7$ are independently H, alkyl, aryl, alkenyl, alkynyl, hydroxy, hydroxyalkyl, alkoxy, mercapto, mercaptoalkyl, alkylthio, amino, alkylamino, aminoalkyl, carboxaldehyde, carboxylic acid and salts thereof, carbalkoxy, alkanoyl, cyano, nitro, halo, trifluoromethyl, alkylsulfonyl, sulfonamido, or $R_1$, $R_5$, $R_6$ and $R_7$ may be taken together with the adjacent group to form a methylenedioxy group.

$R_4$ is H, alkyl, alkenyl, alkynyl, aryl, aralkyl, hydroxy or alkanoyl.

$R_3$ is H, cyano, tetrazolo, carboxaldehyde, hydroxyalkyl, carboxylic acid and salts thereof or derivatives thereof such as esters or amides in which the substituent on the ester oxygen or amide nitrogen is alkyl, aryl, hydroxyalkyl, alkoxyalkyl or amino alkyl.

$R_2$ and $R_8$ are independently H, alkyl, aryl, halo, amino, alkylamino, arylamino, hydroxyamino, hydroxy, alkoxy, mercapto or alkylthio, and X is oxygen, sulfur, imino, and hydroxyimino.

16 Claims, No Drawings

IMIDAZOQUINOXALINE COMPOUNDS

This application is a continuation-in-part of application Ser. No. 283,717, filed July 16, 1981, now abandoned.

The present invention relates to new organic compounds possessing valuable pharmacological activity. In particular, the invention relates to imidazoquinoxalines of the structures:

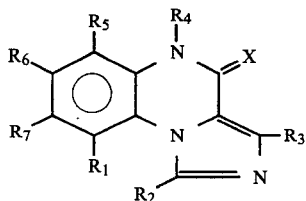

and

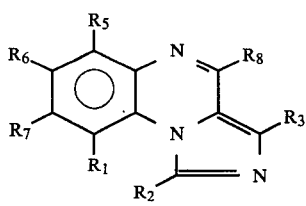

wherein $R_1$, $R_5$, $R_6$ and $R_7$ are independently H, alkyl, aryl, alkenyl, alkynyl, hydroxy, hydroxyalkyl, alkoxy, mercapto, mercaptoalkyl, alkylthio, amino, alkylamino, aminoalkyl, carboxaldehyde, carboxylic acid and salts thereof, carbalkoxy, alkanoyl, cyano, nitro, halo, trifluoromethyl, alkylsulfonyl, sulfonamido, or $R_1$, $R_5$, $R_6$ and $R_7$ may be taken together with the adjacent group to form a methylenedioxy group.

$R_4$ is H, alkyl, alkenyl, alkynyl, aryl, aralkyl, hydroxy or alkanoyl.

$R_3$ is H, cyano, tetrazolo, carboxaldehyde, hydroxyalkyl, carboxylic acid and salts thereof or derivatives thereof such as esters or amides in which the substituent on the ester oxygen or amide nitrogen is alkyl, aryl, hydroxyalkyl, alkoxyalkyl or amino alkyl.

$R_2$ and $R_8$ are independently H, alkyl, aryl, halo, amino, alkylamino, arylamino, hydroxyamino, hydroxy, alkoxy, mercapto or alkylthio, and X is oxygen, sulfur, imino, and hydroxyimino.

The alkyl groups in alkyl per se, hydroxyalkyl, alkoxy, aminoalkyl, alkylamino, alkylthio, mercaptoalkyl, alkanoyl, aralkyl, and carbalkoxy are preferably lower alkyl having from 1 to 8 carbon atoms, more preferably from 1 to 3 carbon atoms, and may be straight chain or branched. These groups include methyl, ethyl, propyl, isopropyl, sec-butyl, iso-amyl, hexyl, 2-ethylhexyl and the like.

The alkenyl and alkynyl groups may be straight chain or branched and preferably have 2 to 8 carbon atoms. These groups include vinyl, propenyl, ethynyl, propinyl and the like.

The preferred compounds are those according to structures I and II wherein $R_6$ and $R_7$ are independently H, alkyl, alkoxy, hydroxy, halo, trifluoromethyl or alkyl sulfonyl.

$R_4$ is H, alkyl, alkenyl, aryl, aralkyl, hydroxy or alkanoyl.

$R_3$ is H, carboxylic acid and salts thereof and esters wherein the group on the ester oxygen is alkyl, alkoxyalkyl or aminoalkyl.

$R_2$ is H, hydroxy, halo, mercapto or alkylthio.

$R_8$ is halo, amino, alkoxy, alkoxy amino, or mercapto.

X is oxygen, sulfur or imino.

$R_1$ and $R_5$ are H.

The compounds of structure I are prepared by the following series of reactions

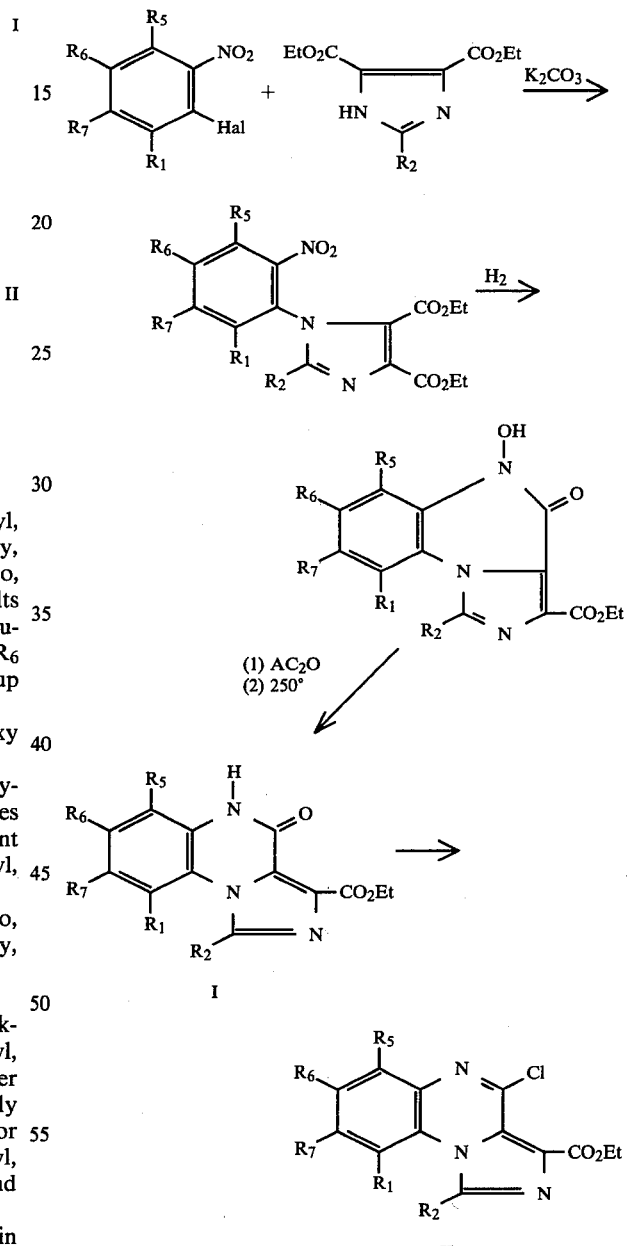

Other standard reactions known in those skilled in the art, such as alkylation, halogenation, nucleophilic displacement reaction, hydrolysis, decarboxylation, etc. etc. can be carried out to modify or introduce other functional groups.

The invention will be more fully understandable from the examples which follow. These examples are given by way of illustration and are not to be considered as limiting.

EXAMPLE 1

A. N-o-Nitrophenylimidazole 4,5-dicarboxylic acid diethyl ester

To a solution of o-fluoronitrobenzene (106 g) and imidazole 4,5-dicarboxylic acid diethyl ester (106 g) in one liter of N,N-dimethyl formamide (DMF) was added anhydrous potassium carbonate (200 g). The reaction mixture was stirred vigorously for at least four hours. After removal of solvent under oil pump vacuum, the residue was treated with water, then extracted with chloroform (300 ml×3). The combined chloroform extracts were washed with water, dried by magnesium sulfate, then concentrated under vacuum to an oil. Upon treatment with ether, the oil was solidified and the product was obtained as a white solid (136 g, 81% yield). Recrystallized from chloroform-hexane, m.p. 93°–95° C.

B. 4-Oxo-4,5-dihydroimidazo[1,5-a]quinoxaline 3-carboxylic acid

The ethanolic solution (250 ml) of N-(o-nitrophenyl)imidazole 4,5-dicarboxylic acid diethyl ester (10 g) with 1 g of catalyst (5% pd/c) was hydrogenated at about 50 psi pressure for one hour. After removal of catalyst, the solution was evaporated under water aspirator vacuum to give the product as an off-white solid (6.2 g, 80% yield). Recrystallized from DMF, m.p. >300° C.

EXAMPLE 2

7-Methylsulfonyl-4-oxo-4,5-dihydroimidazo[1,5-a]quinoxaline 3-carboxylic acid ethyl ester, its 5-hydroxy and 5-acyloxy derivatives The ethanolic solution (1 liter) of 2-(4',5'-dicarbethoxyimidazolo)-5-methylsulfonyl nitrobenzene (12 g) with 0.5 g of catalyst (5% pd/c) was hydrogenated at about 50 psi pressure for one hour. After removal of catalyst, the solution was evaporated under water aspirator vacuum to give a brown colored solid which was characterized as mostly the 5-hydroxy-derivative. This solid was dissolved in boiling acetic anhydride (100 ml) and was refluxed for 10 more minutes. After cooling the 5-acetoxy derivative precipitated out as an off-white crystalline solid (6.2 g, 55% yield). Recrystallized from acetonitrile, m.p. 251°–252° C. When acetic anhydride was substituted by pivaloyl chloride, the pivaloyloxy compound was obtained, m.p. 198°–200° C. The 5-acetyloxy derivative (8 g) was dissolved in boiling Dowtherm (b.p. ~248° C.) and the solution was refluxed for 10 more minutes. After cooling to room temperature, the precipitate was collected, washed with chloroform, then recrystallized from DMF to give the desired 7-methylsulfonyl-4-oxo-4,5-dihydroimidazo[1,5-a]quinoxaline 3-carboxylic acid ethyl ester as an off-white crystalline solid, m.p. >300° C.

EXAMPLE 3

5-Methyl-4-oxo-4,5-dihydroimidazo[1,5-a]quinoxaline 3-carboxylic acid ethyl ester To a solution of 4-oxo-4,5-dihydroimidazo[1,5-a]quinoxaline 3-carboxylic acid ethyl ester (12.4 g) and methyl iodide (98 g) in DMF (1 liter) was added silver oxide (65 g) with stirring. The reaction mixture was stirred at room temperature for 18 hours. After removal of insoluble material the solution was evaporated under oil pump vacuum to dryness. The residue was extracted with chloroform several times. The combined chloroform extracts were washed with water, dried by magnesium sulfate, then evaporated under water aspirator vacuum to give the product as a white solid (8.2 g, 63% yield). Recrystallized from acetonitrile, m.p. 233°–236° C.

EXAMPLE 4

α-5(3-Carbethoxy-4-oxo-4,5-dihydroimidazo[1,5-a]quinoxalyl)acetic acid

α-5(3-Carbethoxy-4-oxo-4,5-dihydroimidazo[1,5-a]quinoxalyl)acetic acid tert-butyl ester (7.9 g) was dissolved in 50 ml of trifluoracetic acid. After standing at room temperature for 18 hours, the solution was evaporated under water aspirator vacuum. The residue was washed with chloroform, then recrystallized from DMF to give the product as a white crystalline solid (5.9 g, 88% yield), m.p. 297°–299° C.

EXAMPLE 5

4-Benzyl and 4-hydroxyethyl-1-[α-5'(3'-carbethoxy-4'-oxo-4',5'-dihydroimidazo[1,5-a]quinoxalyl)acetyl]-piperazines To a solution of compound of Example 4 (3.1 g) and pivaloyl chloride (1.5 g) in DMF (50 ml) was added triethylamine (1.2 g) with stirring. The mixture was stirred at 0° C. for one hour. To this cold mixture, a DMF solution (2 ml) of benzylpiperazine was added and the solution was stirred at 0° C. for another 3 hours. Ether was added to cause the precipitation of a solid which was collected and taken up into chloroform. The chloroform solution was washed with water, dried by magnesium sulfate, then evaporated under vacuum to give the product as a cream colored solid (3.2 g, 69% yield). Recrystallized from DMF, 254°–256° C. By using hydroxyethyl piperazine in place of benzylpiperazine, the corresponding 4-hydroxyethyl derivative was prepared in the same procedure, m.p. 243°–247° C.

EXAMPLE 6

4-Oxo-4,5-dihydroimidazo[1,5-a]quinoxaline 3-carboxylic acid

4-Oxo-4,5-dihydroimidazo[1,5-a]quinoxaline 3-carboxylic acid ethyl ester (3.5 g) was dissolved in 100 ml of 0.5 N sodium hydroxide solution. The solution was heated on steam bath for one hour, cooled to room temperature, then acidified by concentrated hydrochloric acid (5 ml). The product precipitated out as a white solid (3.0 g, 95% yield), m.p. >300° C.

EXAMPLE 7

4-Chloroimidazo[1,5-a]quinoxaline 3-carboxylic acid ethyl ester

4-Oxo-4,5-dihydroimidazo[1,5-a]quinoxaline 3-carboxylic acid ethyl ester (9 g) was suspended in 200 ml of phosphorus oxychloride and the mixture was heated with stirring until it became a clear solution. After cooling to room temperature, the solution was concentrated under vacuum. The residual oil was taken up in chloroform and was put through a short silica gel dry column (chloroform as eluant). The product was obtained from column as an off-white colored solid (4.5 g, 47% yield), m.p. 128°–130° C.

EXAMPLE 8

4-Methoxyimidazo[1,5-a]quinoxaline 3-carboxylic acid methyl ester

To a methanolic solution (250 ml) of 4-chloroimidazo[1,5-a]quinoxaline 3-carboxylic acid ethyl ester (4 g) was added sodium bicarbonate (10 g) with stirring. The mixture was heated on steam bath for 2 hours. After removal of solvent under vacuum, the residue was taken up in water, then extracted with chloroform several times. The combined chloroform extracts were washed with water, dried by magnesium sulfate and evaporated to give the product as an off-white solid (2.2 g, 55% yield). Recrystallized from acetonitrile, m.p. 189°–191° C.

EXAMPLE 9

4-Mercaptoimidazo[1,5-a]quinoxaline 3-carboxylic acid ethyl ester

To an ethanolic solution (200 ml) of 4-chloroimidazo[1,5-a]quinoxaline 3-carboxylic acid ethyl ester (4.8 g) was added thiourea (1.5 g). The mixture was heated on steam bath for one hour. After cooling to room temperature, the precipitated product was collected as a yellowish crystalline solid (3.2 g, 67% yield). Recrystallized from methanol-chloroform, m.p. 251°–253° C.

EXAMPLE 10

4-Carbethoxyhydrazinoimidazo[1,5-a]quinoxaline 3-carboxylic acid ethyl ester

To a solution of 4-chloroimidazo[1,5-a]quinoxaline 3-carboxylic acid ethyl ester (5.5 g) in acetonitrile (120 ml) was added ethyl carbazate (9 g) and triethylamine (20 ml) with stirring. The mixture was refluxed for 18 hours, then evaporated under water aspirator vacuum to dryness. The residue was taken up in chloroform, washed with water, dried by magnesium sulfate, concentrated to a small volume, then put through a silica gel dry column (2% methanol in chloroform as eluant). From column the product was isolated as an off-white solid (4 g, 58% yield). Recrystallized from a mixture of chloroform and hexane, m.p. 126°–128° C.

EXAMPLE 11

4-Amino-7-trifluoromethylimidazo[1,5-a]quinoxaline 3-carboxylic acid ethyl ester A small stream of anhydrous ammonia was passed through a solution of 4-chloro-7-trifluoromethylimidazo[1,5-a]quinoxaline 3-carboxylic acid ethyl ester (5.4 g) in chloroform-ethanol (100 ml each) for 30 minutes. The precipitate was collected and recrystallized from DMF to give the product as an off-white crystalline solid (2.9 g, 57% yield), m.p. >300° C.

EXAMPLE 12

1,4-Dichloroimidazo[1,5-a]quinoxaline 3-carboxylic acid ethyl ester

To a suspension of 4-chloroimidazo[1,5-a]quinoxaline 3-carboxylic acid (2.7 g) in carbon tetrachloride (50 ml) was added N-chlorosuccinimide (3 g) and trace of benzoyl peroxide. The mixture was stirred and refluxed for 48 hours, then evaporated under vacuum to dryness. The residue was taken up in chloroform, washed with water, dried, concentrated to a small volume, then put through a silica gel dry column (chloroform as eluant). From column, the product was obtained as an off-white solid (1.6 g, 50% yield), m.p. 132°–135° C.

EXAMPLE 13

1-Bromo-5-methyl-4-oxo-7-trifluoromethyl-4,5-dihydroimidazo[1,5-a]quinoxaline 3-carboxylic acid ethyl ester To a solution of 5-methyl-4-oxo-7-trifluoromethyl-4,5-dihydroimidazo[1,5-a]quinoxaline 3-carboxylic acid ethyl ester (3.9 g) in carbon tetrachloride (250 ml) was added N-bromosuccinimide (20 g). The mixture was stirred vigorously and was refluxed for 18 hours. After removal of solvent under water aspirator vacuum the residue was chromatographed via a short silica gel dry column (chloroform as eluant). The product was isolated out as an off-white solid (1.9 g, 39% yield). Recrystallized from acetonitrile, m.p. 205°–207° C.

EXAMPLE 14

1-Hydroxy-5-methyl-4-oxo-7-trifluoromethyl-4,5-dihydroimidazo[1,5-a]quinoxaline 3-carboxylic acid ethyl ester To a solution of 1-bromo-5-methyl-4-oxo-7-trifluoromethyl-4,5-dihydroimidazo[1,5-a]quinoxaline 3-carboxylic acid ethyl ester (3.2 g) in dimethylsulfoxide (DMSO) (30 ml) was added potassium acetate (2.5 g) with stirring. The mixture was heated on a steam bath for one hour. Water was then added to cause the precipitation of crude product as a white solid (2.3 g, 85% yield). Recrystallized from a mixture of acetonitrile, chloroform and methanol, m.p. >300° C.

EXAMPLE 15

1-Mercapto-5-methyl-4-oxo-7-trifluoromethyl-4,5-dihydroimidazo[1,5-a]quinoxaline 3-carboxylic acid ethyl ester To an ethanolic solution (200 ml) of 1-bromo-5-methyl-4-oxo-7-trifluoromethyl-4,5-dihydroimidazo[1,5-a]quinoxaline 3-carboxylic acid ethyl ester (1.8 g) was added thiourea (0.4 g). The mixture was refluxed on a steam bath for two hours. After cooling to room temperature, the precipitate was collected, taken up in chloroform and put through a short silica gel dry column (5% methanol in chloroform as eluant). From column, the product was isolated as a white solid (0.7 g, 44% yield). Recrystallized from acetonitrile, m.p. 282° C.

EXAMPLE 16

5-Methyl-1-methylthio-4-oxo-7-trifluoromethyl-4,5-dihydroimidazo[1,5-a]quinoxaline 3-carboxylic acid ethyl ester To a solution of 1-mercapto-5-methyl-4-oxo-7-trifluoromethyl-4,5-dihydroimidazo[1,5-a]quinoxaline 3-carboxylic acid ethyl ester (0.2 g) in dichloromethane was added methyliodide (0.15 g) and triethylamine (0.1 g) with stirring. The mixture was refluxed on a steam bath for one hour, then cooled and washed with water. After drying, the organic phase was evaporated under water aspirator vacuum to give the product as a white solid (0.1 g, 49% yield). Recrystallized from acetonitrile, m.p. 202°–204° C.

EXAMPLE 17

1-Hydroxy-5-methyl-4-oxo-4,5-dihydroimidazo[1,5-a]quinoxaline 3-carboxylic acid

A mixture of 1-bromo-5-methyl-4-oxo-4,5-dihydroimidazo[1,5-a]quinoxaline 3-carboxylic acid ethyl ester (1.5 g) and 0.5 N sodium hydroxide solution (40 ml) was heated on steam bath for 18 hours. After cooling and acidification by concentrated hydrochloric acid, the product precipitated out as a cream colored solid (0.9 g, 81% yield), m.p. >300° C.

EXAMPLE 18

1-Hydroxy-5-methyl-4-oxo-4,5-dihydroimidazo[1,5-a]quinoxaline

1-Hydroxy-5-methyl-4-oxo-4,5-dihydroimidazo[1,5-a]quinoxaline 3-carboxylic acid (0.2 g) was dissolved in boiling di-o-xylylethane (10 ml). The solution was refluxed for 10 minutes then cooled to room temperature. The product precipitated out as a brown solid (0.1 g, 60% yield), m.p. >300° C.

EXAMPLE 19

2,4-Bis-N-4'5'-dicarbethoxy-imidazolonitrobenzene

To a solution of 2,4-difluoronitrobenzene (8 g) and imidazole 4,5-dicarboxylic acid diethyl ester (21.2 g) in DMF (300 ml) was added anhydrous potassium carbonate (40 g). The reaction mixture was vigorously stirred with gentle heating for one hour. After removal of solvent under oil pump vacuum, the residue was treated with water, then extracted with chloroform. The combined chloroform extracts were washed with water, dried by magnesium sulfate, then concentrated under vacuum to an oil. The oil was dissolved in a small volume of chloroform, then put through a short silica gel dry column (chloroform as eluant). From the column, the product was obtained as a cream-colored solid (22.5 g, 42% yield). Recrystallized from chloroform-hexane, m.p. 133°–136° C.

EXAMPLE 20

4-Oxo-5-propyl-4,5-dihydroimidazo[1,5-a]quinoxaline 3-carboxylic acid β-N,N-dimethylaminoethyl ester and its hydrochloride salt A mixture of 4-oxo-5-propyl-4,5-dihydroimidazo[1,5-a]quinoxaline 3-carboxylic acid (1.6 g) and oxalyl chloride (5 ml) in toluene (125 ml) was refluxed overnight. After concentration under vacuum, the residue was taken up in dioxane (75 ml). To this dioxane solution was added triethylamine (10 ml) and N,N-dimethylaminoethanol (3ml). The mixture was stirred at room temperature for one hour, then evaporated under vacuum. The residue was taken up in chloroform, washed with 0.1 N of sodium hydroxide and water. The dried chloroform solution was evaporated to give 0.7 g of 4-oxo-5-propyl-4,5-dihydroimidazo[1,5-a]quinoxaline 3-carboxylic acid β-N,N-dimethylaminoethyl ester as an off-white solid, m.p. 115°–118° C.

The hydrochloride salt was prepared by treating the above free base in methanolic hydrogen chloride. After evaporation and washing with ethylacetate, the salt was obtained as a white solid, m.p. 210° C. (dec).

Following the procedures in the above examples, the following additional intermediates and compounds of the present invention were obtained.

TABLE 1

Intermediates

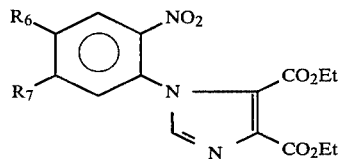

| $R_6$ | $R_7$ | M.P. (°C.) (uncorrected) |
|---|---|---|
| H | H | 93–95 |
| $CH_3$ | H | 76–78 |
| H | $CH_3$ | 110–112 |
| H | F | 139–141 |
| $CF_3$ | H | 108–110 |
| $SO_2CH_3$ | H | 135–138 |
| $NO_2$ | H | 165.5–167.5 |
| H | * | 133–136 |

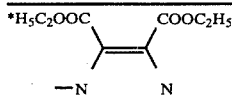

*

TABLE 2

Compounds of the Present Invention Structure I

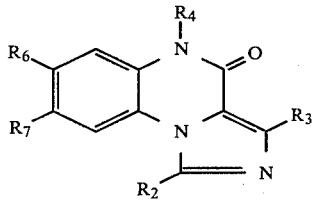

| $R_6$ | $R_7$ | $R_4$ | $R_3$ | $R_2$ | m.p. (°C.) (uncorrected) |
|---|---|---|---|---|---|
| H | H | H | COOEt | H | >300 |
| $CH_3$ | H | H | COOEt | H | >300 |
| H | $CH_3$ | H | COOEt | H | >300 |
| F | H | H | COOEt | H | >300 |
| H | F | H | COOEt | H | >300 |
| $CF_3$ | H | H | COOEt | H | >300 |
| $SO_2CH_3$ | H | H | COOEt | H | >300 |
| $SO_2CH_3$ | H | OH | COOEt | H | 296–298 |

TABLE 2-continued
Compounds of the Present Invention Structure I

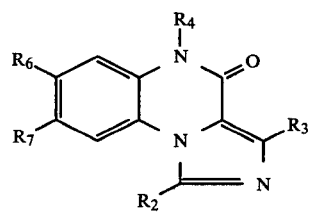

| $R_6$ | $R_7$ | $R_4$ | $R_3$ | $R_2$ | m.p. (°C.) (uncorrected) |
|---|---|---|---|---|---|
| H | ![structure with -N, COOEt, COOEt, N] | OH | COOEt | H | 241–253 |
| $SO_2CH_3$ | H | $OCCH_3$ (O=) | COOEt | H | 251–252 |
| $SO_2CH_3$ | H | $OC-C(CH_3)_3$ (O=) | COOEt | H | 198–200 |
| $CF_3$ | H | $OCCH_3$ (O=) | COOEt | H | 268–270 |
| H | H | $CH_3$ | COOEt | H | 233–236 |
| H | H | $CH_2CH_2CH_3$ | COOEt | H | 160–162 |
| H | H | $CH_2-CH=CH_2$ | COOEt | H | 166–168 |
| H | H | $CH_2$-phenyl | COOEt | H | 217–219 |
| H | H | $CH_2$-(4-Cl-phenyl) | COOEt | H | 218–220 |
| H | H | $CH_2-COOEt$ | COOEt | H | 229–231 |
| H | H | $CH_2COOH$ | COOEt | H | 297–299 |
| H | H | $CH_2-C(O)-N$(piperazine)$N-CH_2$-phenyl | COOEt | H | 254–256 |
| H | H | $CH_2-C(O)-N$(piperazine)$N-CH_2CH_2-OH$ | COOEt | H | 243–247 |
| H | $CH_3$ | $CH_3$ | COOEt | H | 208–210 |
| F | H | $CH_3$ | COOEt | H | 240–243 |
| $CF_3$ | H | $CH_3$ | COOEt | H | 246–248 |
| $CF_3$ | H | $CH_2CH_2CH_3$ | COOEt | H | 223–224.5 |
| $CF_3$ | H | $CH_2$-(4-Cl-phenyl) | COOEt | H | 238–240 |
| Cl | H | $CH_2CH_2CH_3$ | COOEt | H | 233–235 |
| H | H | H | COOH | H | >300 |
| H | $CH_3$ | H | COOH | H | >300 |
| H | H | $CH_3$ | COOH | H | >300 |

TABLE 2-continued
Compounds of the Present Invention Structure I

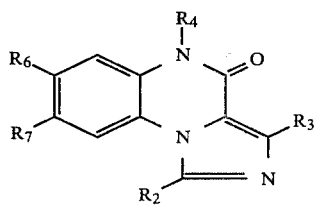

| R$_6$ | R$_7$ | R$_4$ | R$_3$ | R$_2$ | m.p. (°C.) (uncorrected) |
|---|---|---|---|---|---|
| H | H | CH$_2$CH$_2$CH$_3$ | COOH | H | >270 |
| CF$_3$ | H | CH$_3$ | COOH | H | 258–260 |
| CF$_3$ | H | CH$_3$ | COOEt | Br | 205–207 |
| CF$_3$ | H | CH$_3$ | COOEt | OH | >300 |
| CF$_3$ | H | CH$_3$ | COOEt | SH | 282 (dec) |
| CF$_3$ | H | CH$_3$ | COOEt | SCH$_3$ | 202–204 |
| Cl | H | CH$_2$CH$_2$CH$_3$ | COOEt | Br | 154–157 |
| Cl | H | CH$_2$CH$_2$CH$_3$ | COOEt | OH | >270 |
| H | H | CH$_3$ | COOH | OH | >300 |
| Cl | H | CH$_2$CH$_2$CH$_3$ | COOH | OH | >270 |
| H | H | CH$_3$ | H | H | >300 |
| CF$_3$ | H | CH$_3$ | H | H | >300 |
| Cl | H | CH$_2$CH$_2$CH$_3$ | H | OH | >300 |
| H | H | CH$_2$—COO—C(CH$_3$)$_3$ | COOEt | H | 185–187 |
| H | H | CH$_2$CH$_2$CH$_3$ | COOCH$_2$CH$_2$N(CH$_3$)$_2$ | H | 115–118 |

TABLE 3
Compounds of the Structure II

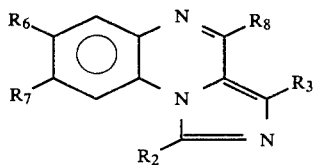

| R$_6$ | R$_7$ | R$_8$ | R$_2$ | R$_3$ | m.p. (°C.) (Uncorrected) |
|---|---|---|---|---|---|
| H | H | Cl | H | COOEt | 128–130 |
| H | H | OCH$_3$ | H | COOMe | 189–191 |
| H | H | OCH$_2$CH$_2$OC$_2$H$_5$ | H | COOEt | 99–102 |
| H | H | SH | H | COOEt | 251–253 |
| H | H | NH—NH—COO—C$_2$H$_5$ | H | COOEt | 216–218 |
| CF$_3$ | H | NH$_2$ | H | COOEt | >300 |
| H | H | Cl | Cl | COOEt | 132–135 |

Certain compounds of the present invention, e.g., those wherein X is O, S or imino while R$_4$ is H, or those wherein R$_2$ is OH or SH, can exist in both keto and enol forms and it is contemplated to include both classes of compounds in the scope of the present invention.

The compounds of this invention are valuable for their cardiotonic activity. They are particularly valuable because the desirable inotropic activity is accompanied by only minimal changes in heart rate and blood pressure.

Activity was measured in an open chest anaesthetized dog model. Drugs were administered intravenously in a polyethyleneglycol-200 suspension over a dose range of 0.1 to 100 mg/kg. Increases in contractile force of up to 49% with maximum increases of only 14% in heart rate were observed.

The compounds can be administered orally in the form of elixirs, tablets and capsules or intraperitoneally, and it will be within the judgment of the physician to determine the optimum dosage and form of administration.

We claim:

1. Imidazoquinoxalines selected from the group consisting of structures I and II

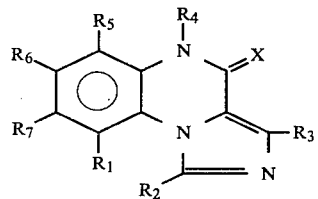

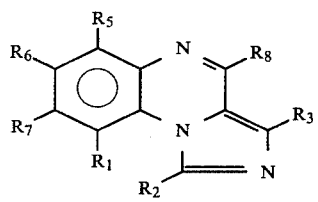

wherein
R$_1$, R$_5$, R$_6$ and R$_7$ are independently H, alkyl, aryl, alkenyl, alknyl, hydroxy, hydroxyalkyl, alkoxy, mercapto, mercaptoalkyl, alkylthio, amino, alkylamino, aminoalkyl, carboxaldehyde,

wherein R$_9$ is H or pharmaceutically acceptable salts, carbalkoxy, alkanoyl, cyano, nitro, halo, trifluoromethyl, alkylsulfonyl, sulfonamido, or R$_1$, R$_5$, R$_6$ or R$_7$ taken together with an adjacent group from a methylenedioxy group;

R$_4$ is H, alkyl, alkenyl, alkynyl, aryl, aralkyl, hydroxy or alkanoyl;

R$_3$ is H, cyano, tetrazolo, carboxaldehyde, hydroxyalkyl or

wherein Y is O or NH and R$_{10}$ is H, alkyl, aryl, hydroxyalkyl, alkoxyalkyl, aminoalkyl or pharmaceutically acceptable salt thereof;

R$_2$ is H, alkyl, halo, amino, alkylamino, arylamino, hydroxyamino, hydroxy, alkoxy, mercapto, or alkylthio;

R$_8$ is alkyl, halo, amino, alkylamino, arylamino, hydroxyamino, hydroxy, alkoxy, mercapto, or alkylthio;

X is oxygen, sulfur, imino, or hydroxyimino;

with the proviso that when R$_2$ is hydroxy it can be in enol or keto form; and wherein the alkyl of the alkyl, hydroxyalkyl, alkoxy, aminoalkyl, alkylamino, alkylthio, mercaptoalkyl, alkanoyl, aralkyl and carbalkoxy contains from 1 to 8 carbon atoms and the alkenyl and alkynyl contain 2 to 8 carbon atoms.

2. The compounds of claim 1 wherein
R$_1$ and R$_5$ are hydrogen;
R$_2$ is hydrogen, hydroxy, halo, mercapto or alkylthio;
R$_3$ is hydrogen,

wherein R$_{10}$ is H, alkyl, alkoxyethyl aminoalkyl or pharmaceutically acceptable salt thereof;

R$_4$ is hydrogen, alkyl, alkenyl, aryl, aralkyl, hydroxy or alkanoyl;

R$_6$ and R$_7$ are independently hydrogen, alkyl, alkoxy, hydroxy, halogen, trifluoromethyl, or alkyl sulfonyl;

R$_8$ is halo, amino, alkoxy, alkoxyamino, or mercapto; and

X is oxygen, sulfur or imino.

3. The compounds of claim 1 wherein the structure is

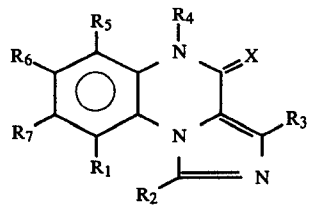

4. The compound of claim 3 which is

7-Chloro-1-hydroxy-4-oxo-5-propyl-4,5-dihydroimidazo-[1,5-a]quinoxaline 3-carboxylic acid β-N,N-dimethylaminoethyl ester and its hydrochloride salt.

5. The compounds of claim 3 wherein
R$_1$ and R$_5$ are hydrogen;
R$_2$ is hydrogen, hydroxy, halo, mercapto or alkylthio;
R$_3$ is hydrogen,

wherein R$_{10}$ is H, alkyl, alkoxyethyl, aminoalkyl or pharmaceutically acceptable salt thereof;

R$_4$ is hydrogen, alkyl, alkenyl, aryl, aralkyl, hydroxy or alkanoyl;

R$_6$ and R$_7$ are independently hydrogen, alkyl, alkoxy, hydroxy, halogen, trifluoromethyl, or alkyl sulfonyl;

R$_8$ is halo, amino, alkoxy, alkoxyamino, or mercapto; and

X is oxygen, sulfur or imino, wherein when R$_2$ is OH it can be in keto or enol form.

6. The compound of claim 3 which is 7-Chloro-1-hydroxy-4-oxo-5-propyl-4,5-dihydroimidazo[1,5-a]quinoxaline 3-carboxylic acid ethyl ester and its pharmaceutically acceptable salts and in both enol and keto form.

7. The compounds of claim 3 wherein
R$_1$ and R$_5$ are hydrogen;
R$_2$ is hydrogen, halo or hydroxy;
R$_3$ is hydrogen,

wherein R$_{10}$ is H, alkyl group having one to three carbons, an aminoalkyl or pharmaceutically acceptable salt thereof;

R$_4$ is hydrogen, hydroxy, alkyl having 1 to 3 carbon atoms, aralkyl having 1 to 3 carbons in the alkyl, alkanoyl or alkoxy having 1 to 3 carbons;

R$_6$ is hydrogen, alkyl having 1 to 3 carbon atoms, trifluoromethyl or alkyl sulfonyl;

R$_7$ is hydrogen or alkyl having 1 to 3 carbon atoms; and

X is oxygen, wherein when R$_2$ is OH it can be in keto or enol form.

8. The compounds of claim 5 wherein
R$_2$ is hydrogen or hydroxy;
R$_3$ is hydrogen,

wherein R$_{10}$ is H, alkyl group having one to three carbons, an aminoalkyl or pharmaceutically acceptable salt thereof;

R$_4$ is an alkyl having one to three carbons;

R$_6$ is hydrogen, halo, or trifluoromethyl;

R$_7$ is hydrogen; and

X is oxygen; wherein when R$_2$ is OH it can be in keto or enol form.

9. The compounds of claim 1 wherein the structure is

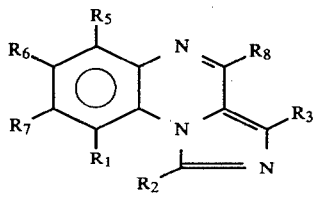

10. The compounds of claim 9 wherein
$R_1$ and $R_5$ are hydrogen;
$R_2$ is hydrogen, hydroxy, halogen, mercapto or alkylthio;
$R_3$ is hydrogen,

wherein $R_{10}$ is H, alkyl, alkoxyethyl, aminoalkyl or pharmaceutically acceptable salts thereof;
$R_6$ and $R_7$ are independently hydrogen, alkyl, alkoxy, hydroxy, halogen, trifluoromethyl, or alkyl sulfonyl; and
$R_8$ is halo, amino, alkoxy, alkoxyamino, or mercapto.

11. The compound of claim 3 which is 7-Chloro-1-hydroxy-4-oxo-5-propyl-4,5-dihydroimidazo[1,5-a]quinoxaline 3-carboxylic acid and its pharmaceutically acceptable salts and in both enol and keto forms.

12. The compounds of claim 9 wherein
$R_2$ is a hydrogen or halogen;
$R_3$ is

wherein $R_{10}$ is $C_1$–$C_3$ alkyl;
$R_6$ is hydrogen or trifluoromethyl;
$R_1$, $R_5$ and $R_7$ are hydrogen, and
$R_8$ is halogen, amino, alkoxy having 1 to 3 carbon atoms or mercapto.

13. The compound of claim 3 which is 5-Methyl-4-oxo-7-trifluoromethyl-4,5-dihydroimidazo[1,5-a]quinoxaline 3-carrboxylic acid ethyl ester and its pharmaceutically acceptable salts.

14. The compound of claim 3 which is 4-Oxo-5-propyl-4,5-dihydroimidazo[1,5-a]quinoxaline 3-carboxylic acid ethyl ester and its pharmaceutically acceptable salts.

15. The compound of claim 3 which is 7-Chloro-4-oxo-5-propyl-4,5-dihydroimidazo[1,5-a]quinoxaline 3-carboxylic acid ethyl ester and its pharmaceutically acceptable salts.

16. The compound of claim 3 which is 7-Chlorol-lhydroxy-4-oxo-5-propyl-4,5-dihydroimidazo[1,5-a]quinoxaline and its pharmaceutically acceptable salts, and in both enol and keto forms.

* * * * *